United States Patent
Abbott, Jr. et al.

(10) Patent No.: US 9,304,095 B2
(45) Date of Patent: Apr. 5, 2016

(54) DOSIMETRY VIA PLATINUM—RUTHENIUM NANOPARTICLE-DECORATED NANOSTRUCTURE

(71) Applicant: Hewlett-Packard Development Company, L.P., Houston, TX (US)

(72) Inventors: James Elmer Abbott, Jr., Corvallis, OR (US); Vittorio Scardaci, Leixlip (IE); Graeme Scott, Leixlip (IE)

(73) Assignee: Hewlett-Packard Development Company, L.P., Houston, TX (US)

( * ) Notice: Subject to any disclaimer, the term of this patent is extended or adjusted under 35 U.S.C. 154(b) by 320 days.

(21) Appl. No.: 13/874,315

(22) Filed: Apr. 30, 2013

(65) Prior Publication Data

US 2014/0320152 A1 Oct. 30, 2014

(51) Int. Cl.
*G01N 27/12* (2006.01)
*G01N 33/00* (2006.01)
*B82Y 30/00* (2011.01)

(52) U.S. Cl.
CPC .............. *G01N 27/127* (2013.01); *B82Y 30/00* (2013.01); *G01N 33/0044* (2013.01)

(58) Field of Classification Search
CPC . G01N 27/122; G01N 27/125; G01N 27/126; G01N 27/127; G01N 27/16; G01N 27/12; G01N 27/4045; G01N 27/004; G01N 27/0044; G07C 9/00896
USPC ......... 324/691, 204, 219, 229, 230; 340/5.61; 422/94; 204/431, 432
See application file for complete search history.

(56) References Cited

U.S. PATENT DOCUMENTS

| | | | |
|---|---|---|---|
| 4,666,859 A * | 5/1987 | Attar ...................... | G01N 31/22 422/413 |
| 8,076,037 B2 | 12/2011 | Perry et al. | |
| 8,247,136 B2 | 8/2012 | Yan et al. | |
| 2005/0145493 A1* | 7/2005 | Saffell et al. .................. | 204/431 |
| 2006/0240245 A1* | 10/2006 | Ishida et al. ............... | 428/312.6 |
| 2007/0114138 A1 | 5/2007 | Krasteva et al. | |
| 2008/0006531 A1* | 1/2008 | Holt .............................. | 204/419 |
| 2008/0038590 A1* | 2/2008 | Nakakubo ....................... | 429/12 |
| 2010/0221148 A1* | 9/2010 | Oie ........................ | G01N 27/16 422/95 |
| 2011/0052805 A1 | 3/2011 | Bordere et al. | |
| 2013/0062211 A1 | 3/2013 | Deshusses et al. | |
| 2013/0260282 A1* | 10/2013 | Yan et al. ...................... | 429/487 |
| 2014/0002239 A1* | 1/2014 | Rayner ......................... | 340/5.61 |
| 2014/0138259 A1* | 5/2014 | Mickelson ......... | G01N 33/0044 205/775 |

FOREIGN PATENT DOCUMENTS

WO 2013002791 A1 1/2013

OTHER PUBLICATIONS

Z. Jiang et al., "Carbnon nanotubes supported metal nanoparticles . . . ," Carbon Nanotubes—Growth and Applications, Dr. Mohammad Naraghi (Ed.), ISBN: 978-953-307-566-2, InTech, DOI: 10.5772/16565. Available from: http://www.intechopen.com, dated Aug. 9, 2011.

* cited by examiner

*Primary Examiner* — Tung X Nguyen
*Assistant Examiner* — David Frederiksen
(74) *Attorney, Agent, or Firm* — Michael A. Dryja

(57) ABSTRACT

A dosimeter includes a platinum-ruthenium (PtRu) nanoparticle-decorated, -coated, or -deposited carbon nanostructure element. The PtRu nanoparticle-decorated carbon nanostructure element is foulably sensitive to a gas.

20 Claims, 2 Drawing Sheets

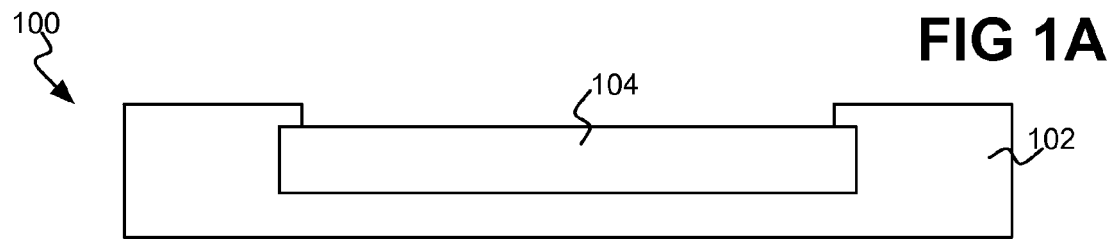
FIG 1A
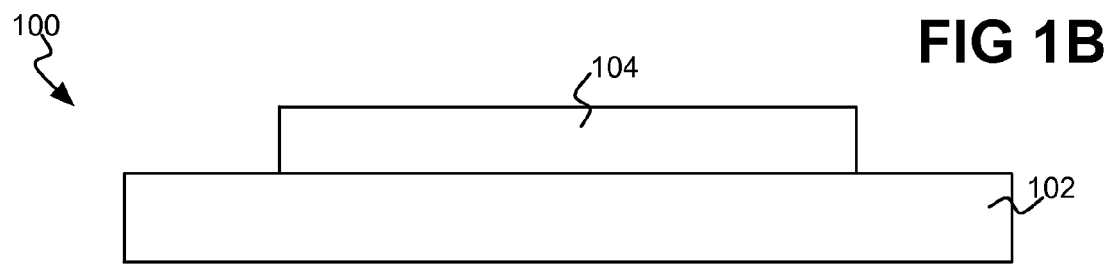
FIG 1B
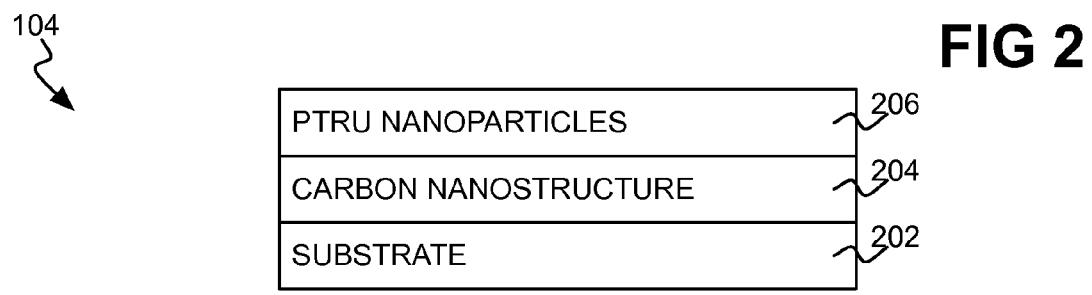
FIG 2
FIG 3
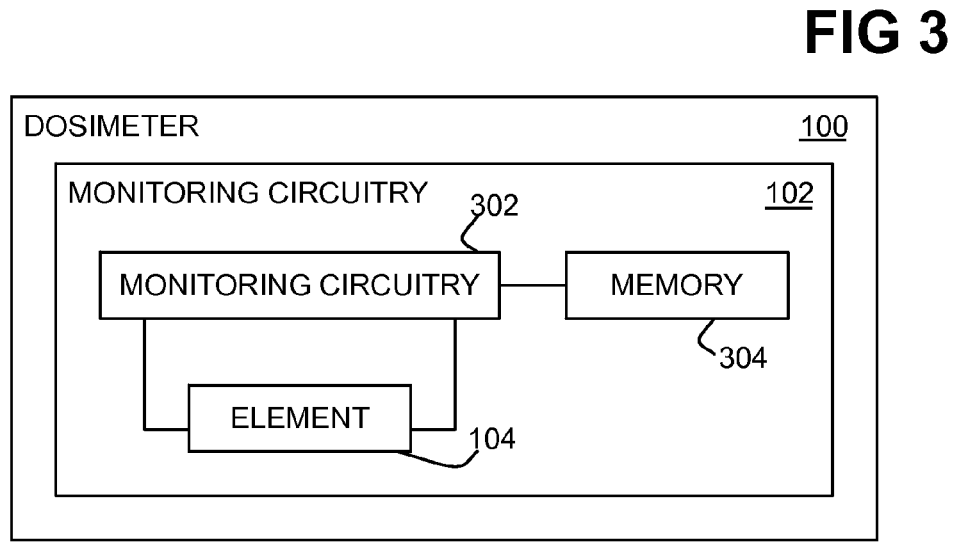

DOSIMETRY VIA PLATINUM—RUTHENIUM NANOPARTICLE-DECORATED NANOSTRUCTURE

BACKGROUND

Hydrogen sulfide gas is present within various industrial and other environments. For instance, within petrochemical and other types of industrial environments, hydrogen sulfide gas may be a byproduct of industrial processes performed within these environments. Hydrogen sulfide gas may further or alternatively be used within industrial processes themselves.

BRIEF DESCRIPTION OF THE DRAWINGS

FIGS. 1A and 1B are diagrams of example hydrogen sulfide dosimeters.

FIG. 2 is a rudimentary diagram of an example platinum-ruthenium (PtRu) nanoparticle-decorated (i.e., PtRu nanoparticle-coated, or PtRu nanoparticle-deposited) carbon nanostructure element usable within a hydrogen sulfide dosimeter.

FIG. 3 is a block diagram of an example hydrogen sulfide dosimeter that includes monitoring circuitry.

DETAILED DESCRIPTION

Figure 4:
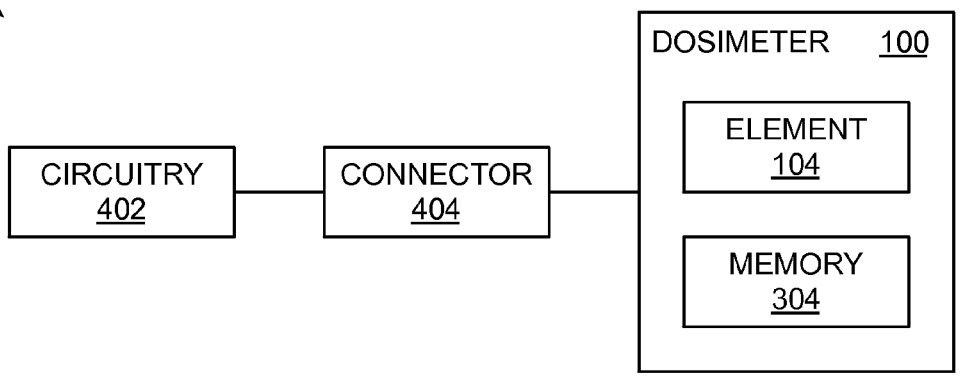
FIG. 4 is a block diagram of an example hydrogen sulfide dosimetry system.

As noted in the background, hydrogen sulfide gas is present within various industrial and other environments. Hydrogen sulfide is highly toxic, and in gas form is flammable. Hydrogen sulfide gas is heavier than air, and tends to accumulate at the bottom of poorly ventilated spaces. Although initially very pungent, hydrogen sulfide deadens the sense of smell, such that personnel exposed to the gas may be unaware of this fact. Acute high-level exposure can result in poisoning, and even death. Chronic low-level exposure can result in fatigue, loss of appetite, headaches, irritability, poor memory, and dizziness. Therefore, when personnel may be potentially exposed to hydrogen sulfide gas, their exposure levels are desirably monitored.

Disclosed herein are techniques for hydrogen sulfide dosimetry that novelly employ a platinum-ruthenium (PtRu) nanoparticle-decorated (i.e., PtRu nanoparticle-coated, or PtRu nanoparticle-deposited) carbon nanostructure element. The carbon nanostructure may be a layer of graphene nanoparticles, flakes, or sheets, a mesh of single wall carbon nanotubes, and/or a mesh of multiple wall carbon nanotubes deposited on a substrate. A layer of PtRu nanoparticles is deposited on this carbon nanostructure.

The PtRu nanoparticle-decorated carbon nanostructure element is foulably sensitive to hydrogen sulfide gas in a normally non-recoverable manner. That is, the element undergoes change as it is exposed to hydrogen sulfide gas, but does not normally revert back to its original state when the element is removed from exposure. In particular, the electrical resistance of the element non-reversibly increases with increased exposure to hydrogen sulfide gas. Total chronic exposure to date can thus be determined by measuring the current electrical resistance of the element, whereas current acute exposure can be determined by measuring a current rate of change in electrical resistance.

However, the PtRu nanoparticle-decorated carbon nanostructure element may be reusable and returned to its original state after having been fouled by exposure to hydrogen sulfide gas. For instance, the element may be subjected to temperature-, chemical-, and other types of processing to revert the element to its original state prior to exposure to hydrogen sulfide gas. Therefore, the PtRu nanoparticle-decorated carbon nanostructure element may be reused and not disposable in some implementations.

FIGS. 1A and 1B show different examples of a hydrogen sulfide dosimeter 100. In each example, the dosimeter includes a housing 102 and a PtRu nanoparticle-decorated (i.e., PtRu nanoparticle-coated or PtRu nanoparticle-deposited) carbon nanostructure element 104. In FIG. 1A, the housing 102 may be a reusable housing fabricated from plastic or another material that does not measurably foul upon repeated exposure to hydrogen sulfide gas. In FIG. 1B, the housing 102 may be a single-use housing fabricated from laminated cardboard or another material that does not measurably foul upon exposure to hydrogen sulfide gas for at least a given duration of time.

In both examples, the PtRu nanoparticle-decorated carbon nanostructure element 104 is externally exposed through the housing 102 to the ambient environment of the dosimeter 100. In FIG. 1A, the element 104 is removably disposed within the housing 102. Therefore, the element 104 can be replaced with a new such element 104 while the same housing 102 is used. For instance, the element 104 may be slidably secured within the housing 102. In FIG. 1B, the element 104 is permanently disposed on the housing 102. Therefore, the housing 102 cannot be reused with a different element 104. For instance, the element 104 may be glued to the housing 102 using a suitable adhesive.

In both examples, the housing 102 is wearable by personnel, such as a user, while in an environment that may potentially include hydrogen sulfide gas. For example, the housing 102 may be a badge or a fob that is worn by the user. The badge or fob may be clipped onto the user's clothing, belt, and so on.

FIG. 2 shows rudimentary depiction of an example of the PtRu nanoparticle-decorated (i.e., PtRu nanoparticle-coated or PtRu nanoparticle-deposited) carbon nanostructure element 104 in detail. The element 104 includes a substrate 202, such as silicon or plastic. A carbon nanostructure 204 is formed on the substrate 202. The carbon nanostructure 204 may be a layer of graphene nanoparticles, nano-flakes, or nano-sheets, a mesh of single wall carbon nanotubes, and/or a mesh of multiple wall carbon nanotubes deposited on the substrate 202. A layer of PtRu nanoparticles 206 is deposited on the carbon nanostructure 204.

In FIG. 2, the layer of PtRu nanoparticles 206 is depicted for purposes of clarity and convenience as being discrete from and on top of the carbon nanostructure 204. In actuality, deposition of the layer of PtRu nanoparticles 206 on the carbon nanostructure 204 can result in the latter resting or forming around the latter. As such, the layer of PtRu nanoparticles 206 may not be as discretely contiguous in relation to the carbon nanostructure 204 as is depicted in FIG. 2.

As noted above, the PtRu nanoparticle-decorated (i.e., PtRu nanoparticle-coated or PtRu nanoparticle-deposited) carbon nanostructure element 104 is foulably sensitive to hydrogen sulfide gas within its environment in a normally non-recoverable and normally non-reversible manner. In particular, the electrical resistance of the element 104 increases with exposure to hydrogen sulfide gas. The element 104 can be employed to determine two types of such exposure: chronic exposure, and acute exposure.

Chronic exposure means the extent to which the PtRu nanoparticle-decorated carbon nanostructure element 104 has been exposed to hydrogen sulfide gas over time. The current electrical resistance of the element 104 correlates to the total exposure of the element 104 to hydrogen sulfide gas. This is because the element 104 is foulably sensitive to hydrogen sulfide gas in a normally non-recoverable and normally non-reversible manner: when the element 104 is removed from an environment that contains hydrogen sulfide, its electrical resistance does not correspondingly decrease. Therefore, the current electrical resistance of the element 104 can be measured at any time to determine the total exposure to hydrogen sulfide gas up to that time.

Acute exposure means the extent to which the PtRu nanoparticle-decorated carbon nanostructure element 104 is currently exposed to hydrogen sulfide gas within a current period of time. The current rate at which the electrical resistance of the element 104 is increasing correlates to the current exposure of the element 104 to hydrogen sulfide gas. This is because the faster the electrical resistance of the element 104 increases, the greater the concentration of hydrogen sulfide gas that is present. Therefore, the current electrical resistance change rate of the element 104 can be measured at a given time to determine the current exposure to hydrogen sulfide gas within the current time period.

For example, it may be desirable to limit total exposure to hydrogen sulfide gas to less than X, and exposure at any given time to less than Y, where Y is less than X. A user may be exposed to hydrogen sulfide gas within four time periods, at exposure levels of A, B, C, and D. If the sum of A, B, C, and D is greater than X, then this means that over time, the user has exceeded the desired total (i.e., chronic) exposure limit to hydrogen sulfide gas, even if none of A, B, C, and D is greater than Y. Furthermore, if any of A, B, C, and D is greater than Y, then this means that in a given time period, the user has exceeded the desired acute exposure limit to hydrogen sulfide gas, even if the sum of A, B, C, and D is less than X. A user can thus exceed either or both of a total chronic exposure limit to hydrogen sulfide gas over time and an acute exposure limit at any given time.

Although the PtRu nanoparticle-decorated carbon nanostructure element 104 undergoes an electrical resistance change responsive to hydrogen sulfide gas exposure, this change in the element 104 may not be outwardly visible to the naked eye. As such, the total chronic exposure to hydrogen sulfide gas may not be able to be determined until the hydrogen sulfide dosimeter 100—or at least the element 104 thereof—is electrically connected to a system to measure the electrical resistance of the element 104, an example of which is presented later in the detailed description. However, the dosimeter 100 can include components to permit a user to view an indication of chronic and/or acute hydrogen sulfide gas exposure without the use of such a system.

FIG. 3 shows a block diagram of such an example hydrogen sulfide dosimeter 100. The dosimeter 100 includes the housing 102 in or on which the PtRu nanoparticle-decorated nanostructure element 104 is disposed, as before. The dosimeter 100 also includes monitoring circuitry 302 disposed within the housing 102, and can further include a memory 304 disposed within the housing 102.

The monitoring circuitry 302 is electrically connectable to the PtRu nanoparticle-decorated nanostructure element 104 to at least periodically indicate the extent of exposure to hydrogen sulfide gas, even while the dosimeter 100 is currently located within an environment containing such gas. The monitoring circuitry 302 may include a display or other indicator in this respect. The monitoring circuitry 302 can measure the current electrical resistance of the element 104 and correlate this resistance to the current total level of hydrogen gas to which the element 104 has been (chronically) exposed over time.

The monitoring circuitry 302 may measure a current rate of electrical resistance change of the PtRu nanoparticle-decorated nanostructure element 104 and correlate this current resistance change rate to the current (acute) level of hydrogen gas to which the element 104 is presently exposed within a current time period. If the memory 304 is present, which may be a non-volatile semiconductor memory or another type of memory, the monitoring circuitry 302 may store the maximum such acute exposure level of hydrogen sulfide gas that has been recorded, for later retrieval and reference. The monitoring circuitry 302 may additionally or alternatively store a history of acute exposure levels as the capacity of the memory 304 permits. In both of these respects, the monitoring circuitry 302 may store values that are the actual acute exposure level(s), or that correlate to these level(s). In the latter case, for example, the monitoring circuitry 302 may just store the measured rate(s) of electrical resistance change of the element 104.

The presence of the monitoring circuitry 302 and optionally the memory 304 increases the functionality of the hydrogen sulfide dosimeter 100, albeit at an increased monetary cost of having to include the circuitry 302 and optionally the memory 304 within the dosimeter 100. However, for environments in which the level of hydrogen sulfide gas can potentially rapidly change and/or exceed the desired acute exposure limit, the wearer of the dosimeter 100 may want to know his or her current exposure level while in such environments. In other scenarios, and/or where cost is an issue, the monitoring circuit 302 and the memory 304 may not be included in the dosimeter 100.

FIG. 4 is a block diagram of an example hydrogen sulfide dosimetry system 400. The system 400 includes circuitry 402 and a connector 404 connected thereto. The system 400 may also include the hydrogen sulfide dosimeter 100. The dosimeter 100 is depicted as including the PtRu nanoparticle-decorated (i.e., PtRu nanoparticle-coated or PtRu nanoparticle-deposited) carbon nanostructure element 104 and can also include the memory 304, as well as other components not shown in FIG. 4.

The connector 404 is receptive to electrical connector of the PtRu nanoparticle-decorated carbon nanostructure element 104 of the dosimeter 100. For instance, the system 400 may be located outside an environment in which hydrogen sulfide exposure is likely to potentially occur. When a user exits this environment, he or she may remove the dosimeter 100 for electrically connecting the element 104 thereof to the system 400. The connector 404 may also be a wireless connector, if the dosimeter 100 has wireless capability. The system 400 can thus be used even when the dosimeter 100 may not have its own circuitry 302 as has been described.

The circuitry 402 measures the extent of exposure to hydrogen sulfide gas of the PtRu nanoparticle-decorated carbon nanostructure element 104. If the dosimeter 100 does not include any memory 304, then the circuitry 402 can measure just the chronic exposure of the element 104 to hydrogen sulfide gas over time, by measuring the current electrical resistance and correlating it to such gas exposure, as has been described. The circuitry 402 may include an indicator, like a display, to indicate this extent of exposure.

If the dosimeter 100 includes a memory 304 that has recorded at least a value corresponding to the level of maximum acute exposure to hydrogen sulfide gas of the PtRu nanoparticle-decorated carbon nanostructure element 104, then the circuitry 402 may read this value from the memory 304. As noted above, the value may be the actual maximum acute exposure level, in which case the circuitry 402 indicates the level on its indicator. The value may just be the maximum rate of electrical resistance change of the element 104, in which case the circuitry 402 correlates this resistance change rate to the a level of exposure to hydrogen sulfide gas.

Figure 5:
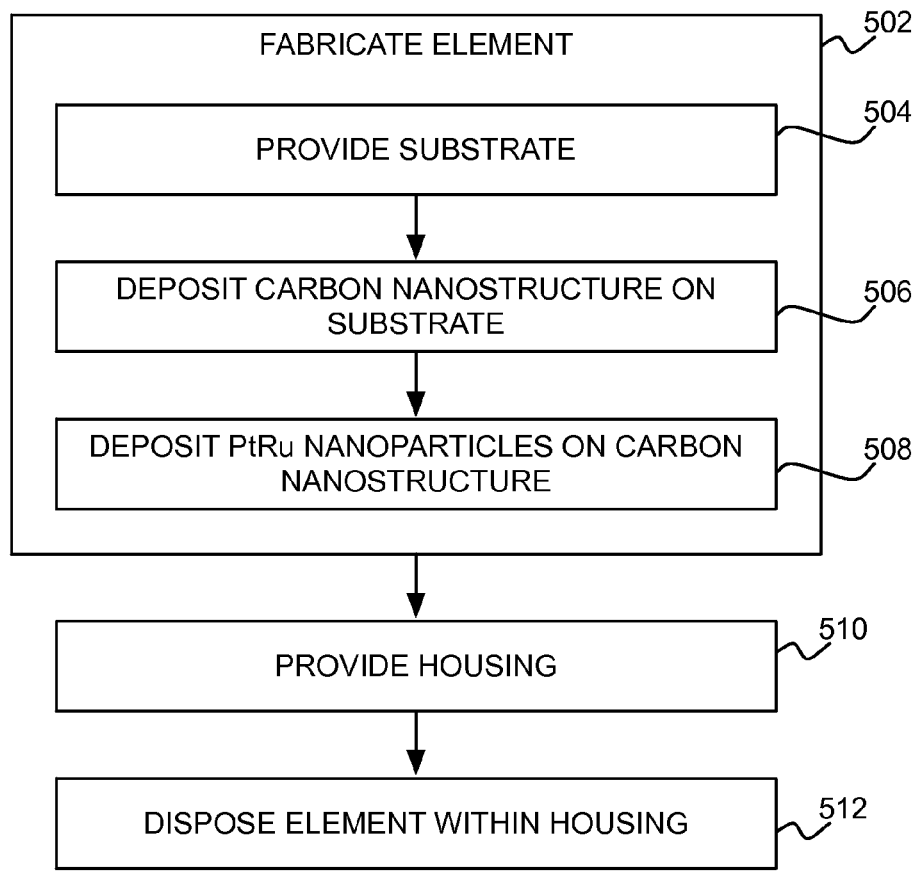
FIG. 5 is a flowchart of an example method for manufacturing a hydrogen sulfide dosimetry system.

FIG. 5 shows an example method 500 of manufacture of a hydrogen sulfide dosimeter 100. The PtRu nanoparticle-decorated (i.e., PtRu nanoparticle-coated or PtRu nanoparticle-deposited) carbon nanostructure element 104 is fabricated (502). Such fabrication can in one implementation include providing the substrate 202 (504), depositing the carbon nanostructure on the 202 (506), and then depositing the layer of PtRu nanoparticles 206 on the carbon nanostructure 204 (508). Other implementations are also amenable to utilization with the techniques disclosed herein. As one example, the PtRu nanoparticles 206 may be mixed into a suspension with the carbon nanostructure 204, and the resulting mixture deposited on the substrate 202 to realize the PtRu nanoparticle-decorated carbon nanostructure element 104. The method 500 further includes providing the housing 102 that has been described (510), and concludes by removably or permanently disposing the element 104 within the housing 102 (512).

The techniques disclosed herein have been described in relation to a PtRu nanoparticle-decorated carbon nanostructure element that is foulably sensitive to hydrogen sulfide gas. However, the techniques are applicable to such an element being foulably sensitive to other gases. In general, then, the techniques disclosed herein encompass dosimetry using a PtRu nanoparticle-decorated carbon nanostructure element that is foulably sensitive to a gas, such as hydrogen sulfide gas.

We claim:

1. A dosimeter comprising:
a housing;
a platinum-ruthenium (PtRu) nanoparticle-decorated carbon nanostructure element disposable within or on the housing and externally exposable through the housing to an ambient environment in which the housing is locatable,
wherein the PtRu nanoparticle-decorated carbon nanostructure element is configured to detect presence of a gas within the ambient environment by being foulably sensitive to the gas in that an electrical resistance of the PtRu nanoparticle-decorated carbon nanostructure element cumulatively increases with increasing exposure of the PtRu nanoparticle-decorated carbon nanostructure element to the gas.

2. The dosimeter of claim 1, wherein the gas to which the PtRu nanoparticle-decorated carbon nanostructure element is foulably sensitive is hydrogen sulfide gas.

3. The dosimeter of claim 1, further comprising:
monitoring circuitry disposed within the housing to measurably monitor the PtRu nanoparticle-decorated carbon nanostructure element to at least periodically indicate an extent of exposure to the gas while the housing is currently located within the ambient environment.

4. The dosimeter of claim 3, wherein the extent of exposure to the gas comprises an acute exposure to the gas within a current time period,
and wherein the monitoring circuitry is to measure a current rate of electrical resistance change of the PtRu nanoparticle-decorated carbon nanostructure element and correlate the current rate of electrical resistance change to a current level of the acute exposure to the hydrogen gas within the current time period.

5. The dosimeter of claim 3, wherein the extent of exposure to the gas comprises a maximum acute exposure to the gas within any time period,
and wherein the dosimeter further comprises a memory to store a level of the maximum acute exposure to the gas within any time period.

6. The dosimeter of claim 3, wherein the extent of exposure to the gas comprises a chronic exposure to the gas over time,
and wherein the monitoring circuitry is to measure a current electrical resistance of the PtRu nanoparticle-decorated carbon nanostructure element and correlate the current electrical resistance to a current level of the chronic exposure to the hydrogen gas over time.

7. The dosimeter of claim 1, wherein at least the PtRu nanoparticle-decorated carbon nanostructure element is connectable to measuring circuitry outside the ambient environment in which the gas is present,
and wherein the measuring circuitry is to measure and indicate an extent of exposure to the gas while the housing was previously located within the ambient environment.

8. The dosimeter of claim 1, wherein at least the PtRu nanoparticle-decorated carbon nanostructure element is replaceably removable from the housing.

9. The dosimeter of claim 1, wherein the PtRu nanoparticle-decorated carbon nanostructure element comprises:
a substrate;
a carbon nanostructure deposited on the substrate and comprising one or more of a layer of graphene nanoparticles, flakes, or sheets, a mesh of single wall carbon nanotubes, and a mesh of multiple wall carbon nanotubes; and
a layer of PtRu nanoparticles deposited on the carbon nanostructure.

10. The dosimeter of claim 1, wherein the housing comprises a wearable housing that a user is to wear while in the ambient environment.

11. The dosimeter of claim 1, wherein when the gas is no longer present within the ambient environment, the electrical resistance of the PtRu nanoparticle-decorated carbon nanostructure element does not correspondingly decrease, such that a current value of the electrical resistance is measurable at any time to determine a total exposure to the gas up to a present time.

12. A dosimetry system comprising:
a connector receptive to electrical connection of a platinum-ruthenium (PtRu) nanoparticle-coated carbon nanostructure element of a dosimeter, the PtRu nanoparticle-coated carbon nanostructure element foulably sensitive to a gas within an environment in that the element remains in a fouled state after removal from exposure to the gas; and
circuitry to measure an extent of exposure to the gas while the PtRu nanoparticle-coated carbon nanostructure element was previously located within the environment by measuring an electrical resistance of the PtRu nanoparticle-coated carbon nanostructure element.

13. The dosimetry system of claim 12, wherein the gas to which PtRu nanoparticle-coated carbon nanostructure is foulably sensitive is hydrogen sulfide gas.

14. The dosimetry system of claim 12, wherein the circuitry comprises an indicator to indicate the extent of exposure measured by the circuitry.

15. The dosimetry system of claim 12, wherein the extent of exposure to the gas comprises a chronic exposure to the gas over time, and wherein the monitoring circuitry is to measure a current electrical resistance of the PtRu nanoparticle-coated carbon nanostructure element and correlate the current electrical resistance to a current level of the chronic exposure to the hydrogen gas over time.

16. The dosimetry system of claim 12, wherein the extent of exposure to the gas comprises a maximum acute exposure to the gas within any time period, and wherein the circuitry is to read a memory of the dosimeter in which a value corresponding to a level of the maximum acute exposure to the gas within any time period is stored.

17. The dosimetry system of claim 16, wherein the value is the level of the maximum acute exposure to the gas within any time period.

18. The dosimetry system of claim 16, wherein the value is a maximum rate of electrical resistance change of the PtRu nanoparticle-coated carbon nanostructure element within any time period, and wherein the circuitry is to correlate the maximum rate of electrical resistance change to the level of the maximum acute exposure to the hydrogen gas within any time period.

19. The dosimetry system of claim 12, further comprising the dosimeter.

20. A method for manufacturing a dosimeter comprising:
providing a housing of the dosimeter; and
disposing a platinum-ruthenium (PtRu) nanoparticle-deposited carbon nanostructure element within or on the housing such that the PtRu nanoparticle-deposited carbon nanostructure element is externally exposed through the housing,
wherein the PtRu nanoparticle-deposited carbon nanostructure element is configured to detect presence of a gas within an ambient environment by being foulably sensitive to the gas in that an electrical resistance of the PtRu nanoparticle-decorated carbon nanostructure element cumulatively increases with increasing exposure of the PtRu nanoparticle-decorated carbon nanostructure element to the gas.

* * * * *